US 11,992,664 B2

(12) United States Patent
Rooker et al.

(10) Patent No.: US 11,992,664 B2
(45) Date of Patent: May 28, 2024

(54) DEVICE FOR ROTATING AN OBJECT

(71) Applicant: Sharpfield Holding B.V., Rotterdam (NL)

(72) Inventors: Marc-Dennis Rooker, Kampen (NL); Robin Jordy Kuipers, Kampen (NL); Lucas Jan Bolier, Kampen (NL)

(73) Assignee: SHARPFIELD HOLDING B.V., Rotterdam (NL)

( * ) Notice: Subject to any disclaimer, the term of this patent is extended or adjusted under 35 U.S.C. 154(b) by 791 days.

(21) Appl. No.: 15/734,524

(22) PCT Filed: Jun. 4, 2019

(86) PCT No.: PCT/NL2019/050326
§ 371 (c)(1),
(2) Date: Dec. 2, 2020

(87) PCT Pub. No.: WO2019/235917
PCT Pub. Date: Dec. 12, 2019

(65) Prior Publication Data
US 2021/0228816 A1 Jul. 29, 2021

(30) Foreign Application Priority Data

Jun. 4, 2018 (NL) ..................... 2021051

(51) Int. Cl.
*A61M 5/32* (2006.01)

(52) U.S. Cl.
CPC ... *A61M 5/3205* (2013.01); *A61M 2005/3208* (2013.01); *A61M 2205/14* (2013.01); *A61M 2205/3327* (2013.01); *A61M 2205/52* (2013.01)

(58) Field of Classification Search
CPC ........ A61M 5/3205; A61M 2005/3208; A61M 2205/14; A61M 2205/3327; A61M 2205/52; A61M 5/3276
See application file for complete search history.

(56) References Cited

U.S. PATENT DOCUMENTS

| | | | |
|---|---|---|---|
| 4,807,344 A * | 2/1989 | Kelson | A61M 5/3205 29/240 |
| 5,188,598 A * | 2/1993 | Thead | A61M 5/3205 604/110 |
| 5,482,297 A | 1/1996 | Burns et al. | |

FOREIGN PATENT DOCUMENTS

| | | |
|---|---|---|
| EP | 0838228 A3 | 5/1998 |
| JP | 09-224985 A | 9/1997 |

OTHER PUBLICATIONS

International Search Report and Written Opinion of the International Searching Authority dated Sep. 26, 2019 issued in corresponding International Patent Application No. PCT/NL2019/050326 (9 pgs.).

* cited by examiner

*Primary Examiner* — James D Ponton
(74) *Attorney, Agent, or Firm* — Steven M. Kochler; Westman, Champlin & Koehler, P.A.

(57) ABSTRACT

Stabbing accidents are prone to occur to people handling needles, for example when recapping a needle or when trying to remove a needle from a syringe. A device is provided for safe and automatic removal of a needle from a syringe aimed to prevent stabbing accidents. The device is arranged to grab hold of and rotate the needle of a syringe. The needle, after being rotate off the syringe is discarded into the device by releasing the grip on the needle. The device rotates two rotating gears relative to each other to move grippers towards the needle, and rotates the two gears together to rotate the needle relative to the syringe which may be held by the user.

12 Claims, 4 Drawing Sheets

DEVICE FOR ROTATING AN OBJECT

CROSS-REFERENCE TO RELATED APPLICATIONS

This application is the U.S. National Stage of PCT/NL2019/050326, filed Jun. 4, 2019, which claims priority to: Netherlands Patent Application No. 2021051, filed Jun. 4, 2018, the entire contents of both of which are herein incorporated by reference in their entireties.

FIELD OF THE INVENTION

The invention relates to the field of devices arranged for rotating objects and for removing needles from syringes in particular.

BACKGROUND

Syringes, for example used in medical application, often comprise a screw head for screwing a disposable needle on the syringe. When removing the needle from the syringe after use, a user such as a doctor or nurse may accidentally puncture their own skin with the needle which may be contaminated with a patients blood and/or a medicine.

Putting back of a cap over a used needle, known as recapping, is dangerous as well. Often recapping is done by holding the needle in one hand and attempting to place a small cap held in the other hand on the needle. When recapping, the needle could miss the cap and stab the hand holding the cap and the needle could pierce the cap and stab the hand holding the cap. Additionally, a poorly fitting cap could slip off a recapped needle and stab the hand holding the cap.

SUMMARY

It is preferred to provide a safer and more easy to use device for rotating an object, for example rotating a needle of a syringe.

A first aspect provides a device for rotating an object like the cuff of a needle, the device comprising a rotation mechanism. The rotation mechanism comprises a first rotatable gripper hub arranged to be driven by a first driving unit comprised by the device. The first gripper hub comprises a first central opening and the first rotatable gripper hub is arranged to be rotated around an axis of rotation. The rotation mechanism further comprises a second rotatable gripper hub arranged to be driven by a second driving unit comprised by the device. The second gripper hub comprises a second central opening aligned with the first central opening and the second rotatable gripper hub is arranged to be rotated around the axis of rotation.

The rotation mechanism further comprises a first gripper unit and a second gripper unit, each having a gripping section for engaging with the object. The first gripper unit and the second gripper unit are mounted to the first gripper hub and the second gripper hub such that if the first gripper hub is rotated relative to the second gripper hub, the gripping sections move towards the axis of rotation.

The device further comprising a controller arranged to operate one of the first driving unit and the second driving unit such that the first gripping hub is rotated relative to the second gripping hub in a first direction for moving the first gripping section and the second gripping section towards the axis of rotation. The controller is further arranged to operate the first driving unit and the second driving unit such that the first gripper hub and the second gripper hub rotate at substantially the same annular speed around the axis of rotation.

The needle and the cuff are received in the aligned openings. Subsequently, this device firstly grips the cuff by means of the grippers, following the first rotating action. The grippers may remain more or less at one and the same angular position relative to the cuff and/or the syringe. By the next rotating action, the grippers execute a rotating action relative to a centre line of the opening, thus rotating the cuff of the needle. With the syringe kept in place, the cuff is twisted off the syringe.

In an embodiment of the device, the controller is even further arranged to operate one of the first driving unit and the second driving unit such that the first gripping hub is rotated relative to the second gripping hub in a second direction for moving the first gripping section and the second gripping section substantially radially away from the axis of rotation.

The device allows a user to remove the needle of a syringe with a minimal to none risk of stabbing himself with the sharp end of the needle, which may be contaminated with blood, medicine or any other harmful material. During the entire use of the device, the sharp end of the needle may be pointed away from the user, more specifically pointed away from a hand which when recapping would be in line with the movement direction of the needle.

The device may be arranged such that at least one of the first driving unit and the second driving unit is arranged to engage with the first gripper hub and the second gripper hub, respectively, via a biasing element, such that the gripping sections are biased away from the axis of rotation.

The biasing element may be a spring operationally provided between the at least one of the first driving unit and the second driving unit and the first gripper hub and the second gripper hub, respectively.

The at least one of the first driving unit and the second driving unit is arranged to drive a gear and is connected to the gear through a biasing element and the corresponding gripper hub is provided with a circular rack arranged to engage with the gear.

The controller may be arranged to operate the one of the first driving unit and the second driving unit in the first direction for moving the first gripping section and the second gripping section towards the axis of rotation by a pre-determined distance.

An embodiment of the device comprises a torque sensing module for determining a torque applied by the one of the first driving unit and the second driving unit. In such an embodiment of the device, the controller may be arranged to operate the one of the first driving unit and the second driving unit in a first direction for moving the first gripping section and the second gripping section towards the axis of rotation until the torque reaches a pre-determined value.

The device may comprise a memory for storing an amount of rotational movement of the one of the first driving unit and the second driving unit until the torque reaches the pre-determined value.

When the first driving unit and the second driving unit are operated such that the first gripper hub and the second gripper hub move at substantially the same annular speed, the first gripper hub and the second gripper hub may move in the first direction.

The first gripping unit and the second gripping unit may be rotatably connected to a first of the first gripper hub and the second gripper hub and slidably connected to a second of the first gripper hub and the second gripper hub.

In an embodiment of the device, the first gripping unit and the second gripping unit are slidably mounted to a first of the first gripper hub and the second gripper hub such that a substantially straight and radially oriented sliding trajectory is provided when the first gripper hub is rotated relative to the second gripper hub. Furthermore, the first gripping unit and the second gripping unit are slidably mounted to a second of the first gripper hub and the second gripper hub such that a curved substantially eccentric trajectory is provided when the first gripper hub is rotated relative to the second gripper hub.

The device may comprise a sensor for detecting if an object has been provided to the device.

DESCRIPTION OF THE FIGURES

The various aspects and embodiments thereof will now be discussed in further detail in conjunction with drawings. In the drawings, FIG. 1 A shows an embodiment of a device for rotating an object;

FIG. 1 B shows a section view of the device;

FIG. 2 B shows the rotation mechanism;

FIG. 2 C shows a schematic representation of the device; and

FIG. 2 D shows an exploded view of the rotation mechanism.

DETAILED DESCRIPTION OF THE EMBODIMENTS

FIG. 1A shows an embodiment of a device 100 for rotating an object, comprising an outer opening 102 provided in a housing 104. The outer opening 102 is arranged for receiving at least part of the object that is to be rotated.

The device 100 comprises a controller arranged to operate the device 100 to engage with the object that is to be rotated, rotate the object, and disengage the object. Details on how the object is engaged, rotated and disengaged will be discussed below.

FIG. 1B shows a section view of an embodiment of the device 100. Provided inside the housing 104 and aligned with the outer opening 102 is a rotation mechanism 200 arranged for engaging and rotating the object inserted in the outer opening 102. At least part of the outer opening 102 may be tapered towards the inside of the housing 104 thus providing a wide opening which may increase the ease of inserting the object that is to be rotated.

Figure 1:
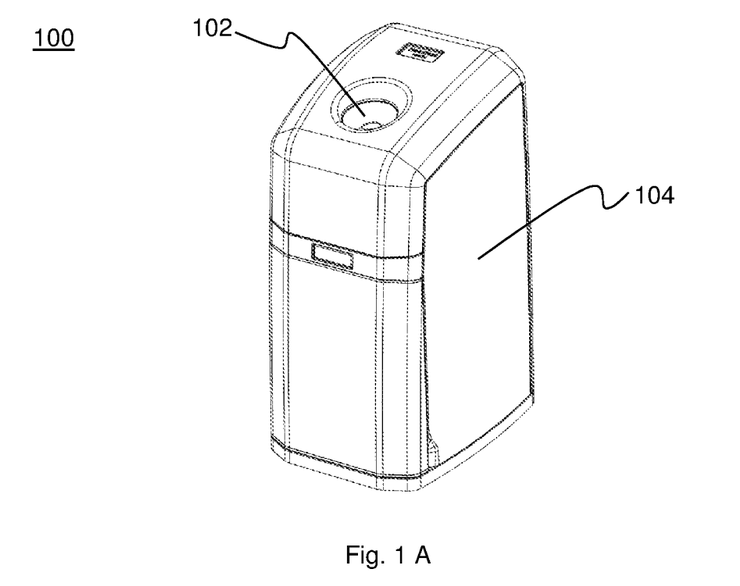

The device 100 comprises a first driving unit and a second driving unit for driving the rotation mechanism 200; FIG. 1 B shows the second driving unit 114 connected to a second driving gear 124 for engaging with the rotation mechanism 200. Operation of the driving units is controlled by the controller 130.

The object to be rotated may be a needle provided on a syringe, wherein a first of the needle and the syringe comprises an outer thread arranged to engaged with an inner thread comprised by the other of the needle and the syringe. It may be an object of the device 100 to rotate the needle relative to the syringe in a direction which removes the needle from the syringe. When removed, the needle may fall down through a funnel 106 provided in the housing 104 which leads to a storage container 108 arranged for storing one or more needles.

The device 100 may be provided with a sensor 110 arranged to detect whether an object has been inserted into the device 100 through the outer opening 102. The sensor 110 may be an optical sensor provided with a light source and a light detector. The sensor 110 may provide a signal to the controller which indicates that an object has been inserted in to device 100 and may be rotated. The controller in turn may be arranged for receiving said signal. In an alternative embodiment, the sensor 110 is arranged as a mechanical switch, which may be activated by the insertion of the object into the outer opening 102.

FIG. 2A shows a detailed view of an embodiment of the rotation mechanism 200 provided with the outer opening 102 in a mechanism housing 203. The rotation mechanism 200 comprises a first rotatable gripper hub 202 and a second rotatable gripper hub 204. The first rotatable gripper hub 202 is arranged to be driven by the first driving unit and the second rotatable gripper hub 204 is arranged to be driven by the second driving unit 114.

Operation of the device 100 will now be discussed in conjunction with FIG. 2B which shows the rotation mechanism 200 without the mechanism housing 203 and outer opening 102. FIG. 2C shows a schematic representation of active components of the device 100.

Figure 2:
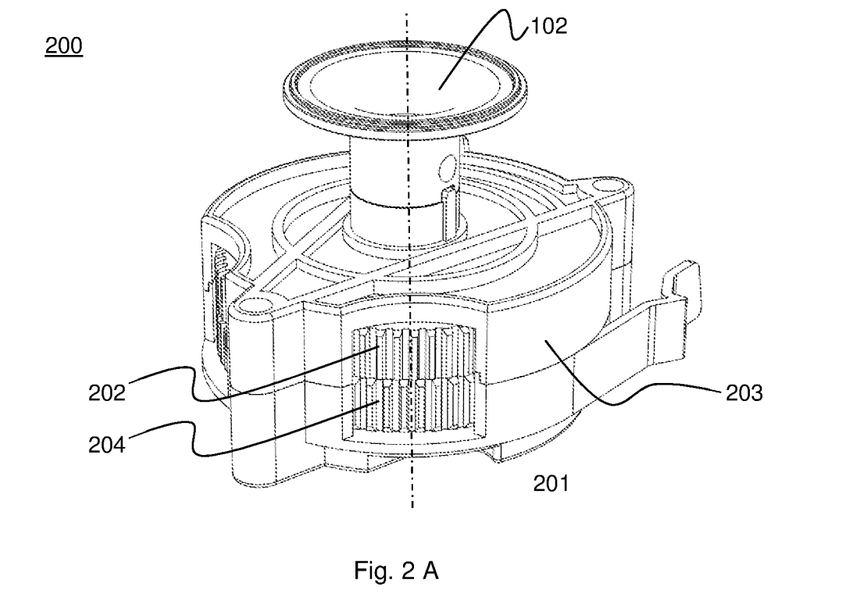

FIG. 2 C shows the controller 130 connected to the sensor 110. The controller is further connected to the first driving unit 112 that is connected to a first driving gear 122 and the second driving unit 114 that is connected to the second driving gear 124 via an optional biasing element 290.

During a first operation step, the first gripper hub 202 is rotated relative to the second gripper hub 204 in a first direction around an axis of rotation 201 causing gripping sections 216 to be moved towards the axis of rotation 201. The movement of the gripping sections 216 allows the rotation mechanism 200 to engage the object that is to be rotated.

The first operating step is arranged to clamp the object that is to be rotated between the gripping sections 216 and is started when an object is detected in the device 100, for example by the sensor 110, or when another trigger is given, such as a user input using a button, lever, foot pedal, or any other trigger.

The controller is furthermore arranged to, in a second operating step, operate the first driving unit 112 and the second driving unit 114 such that the first gripper hub 202 and the second gripper hub 204 rotate at substantially the same annular speed around the axis of rotation 201, preferably at the same annular speed. The rotation of the first gripper hub 202 and the second gripper hub 204 may be in the first direction, for example clockwise, or in the second direction, for example counter-clockwise.

Since the object has been gripped in the first operation step, prior to the second operation step, the object will be rotated with the same annular speed as the gripper hubs during the second operation step.

The substantially same annular speed or preferred same annular speed of the first gripper hub 202 and the second gripper hub 204 may be achieved by the controller 130 feeding the same control signal to the first driving unit 112 and the second driving unit 114. The first driving unit 112 and second driving unit 114 may be arranged as stepper motors, DC motors with or without brushes, or any other type of motor capable of producing a rotational motion.

Finally, for the third operation step, the controller 130 is arranged to operate one of the first driving unit 112 and the second driving unit 114 in a second direction for disengaging the object. The operation of one of the first driving unit 112 and the second driving unit 114 results in a rotation of the first gripper hub 202 with respect to the second gripper hub 204 in a second direction. This in turn causes the gripping sections 216 to move substantially racially away from the axis of rotation 201, thus disengaging from the object. The disengaged object may fall down into the container 108 of the device optionally through the funnel 106. The third operation step may in embodiments of the device 100 comprising a biasing element be optional, as will be elaborated on further on in the description.

The third step of disengaging the object may be triggered by a user input such a operating a button, lever, foot pedal, touch screen, or any other input. Alternatively, when the needle is removed from the syringe, the user may pull the syringe out of the outer opening 102. This pulling out may cause the sensor 110 to stop detecting that an object has been provided into the device 100, which in turn may cause the controller to perform the third operation step.

Figure 2D:
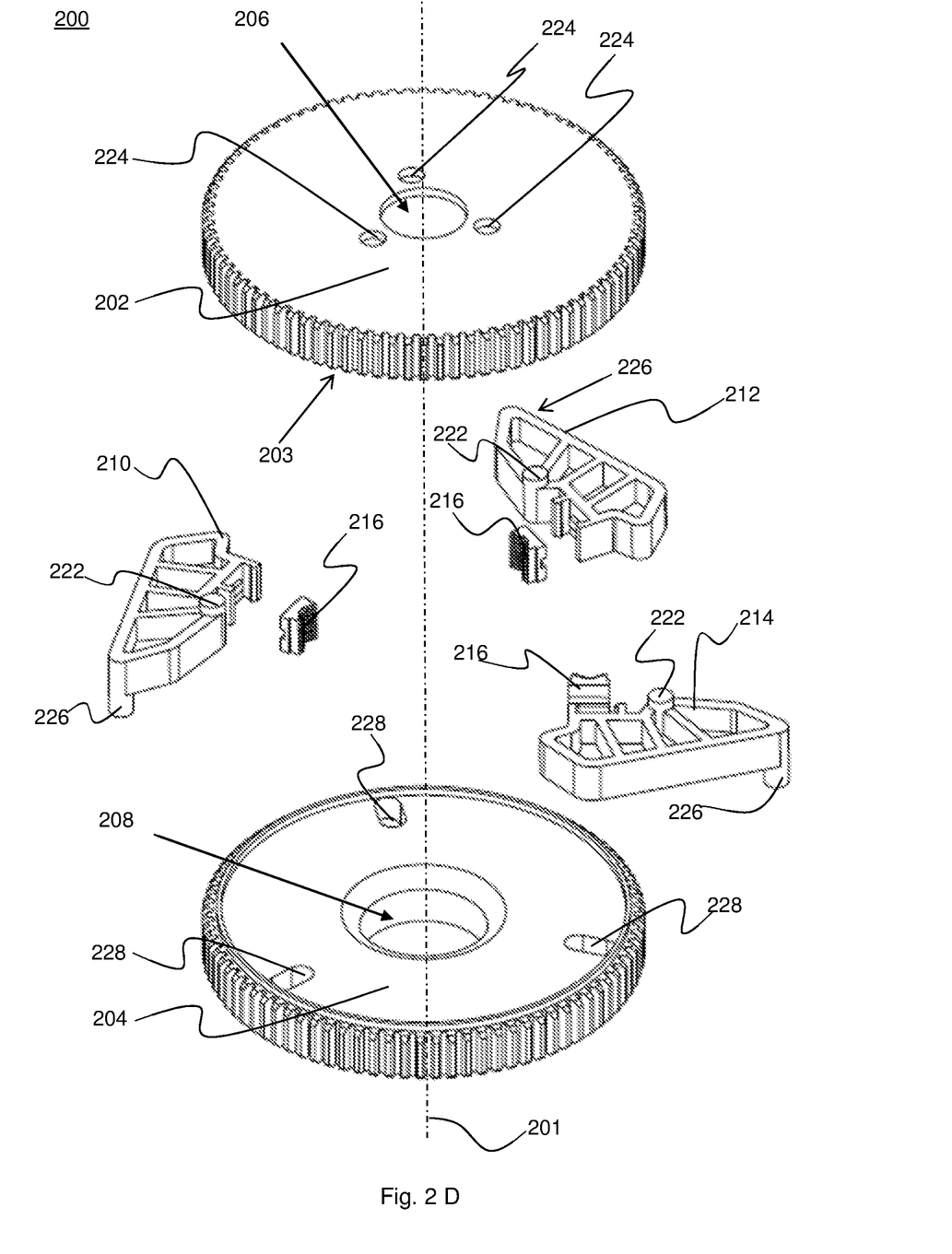

FIG. 2 D will be used to explain in more detail an embodiment of how the gripping sections 216 are engaged or disengaged from the object. FIG. 2 D shows an exploded view of the rotation mechanism 200 comprising the first rotatable gripper hub 202 and the second rotatable gripper hub 204. The first rotatable gripper hub 202 comprises a first central opening 206 and the second rotatable gripper hub 204 comprises a second central opening 208 aligned with the first central opening 206. The first central opening 206 and the second central opening 208 are arranged for receiving at least part of the object that is to be rotated.

The rotation mechanism 200 further comprises a first gripper unit 210, a second gripper unit 212 and an optional third gripper unit 214, each provided with a gripping section 216 for engaging with the object to be rotated. The gripper section 216 is preferably provided with a surface arranged for improved engagement with the object to be gripped. The improved engagement may be provided by a high friction material or with a set of teeth provided on the surface.

In an embodiment of the rotation mechanism 200 comprising three gripper units, the gripper units may be spaced 120 degrees apart from each other. Embodiments of the rotation mechanism 200 comprising two, four or more gripper units are also envisioned, wherein the gripper units may be spaced equiangularly apart from each other.

To accommodate the gripper units when the rotation mechanism 200 is assembled, that is when the first rotatable gripper hub 202 is provided at a substantially small distance from the second rotatable gripper hub 204, the substantially small distance being smaller than a thickness of a gripper unit, at least one of the first rotatable gripper hub 202 and the second rotatable gripper hub 204 may be provided with a cavity 203 arranged for accommodating at least part of a gripper unit.

In the embodiment as shown in FIG. 2 D, the cavity 203 is provided by the first rotatable gripper hub 202 at a side arranged to be placed nearest to the second rotatable gripper hub 204. At least one of the gripper hubs comprises in this embodiment a deepened part. If the gripper hubs are placed on top of one another, with the central openings aligned and the at least one deepenings facing the other gripper hub, the cavity 203 is formed by the at least one deepening.

In an embodiment of the rotation mechanism 200, each gripper unit comprises a first protrusion 222 arranged for being at least partially inserted into a hole 224 comprised by the first rotatable gripper hub 202. In an embodiment of the rotation mechanism 200 comprising three gripper units, the first rotatable gripper hub 202 thus comprises three holes 224.

In the embodiment of the rotation mechanism 200 wherein each gripper unit comprises a first protrusion 222, each gripper unit also comprises a second protrusion 226 provided at an opposite side of the gripper unit than the first protrusion 222. A second protrusion 226 is arranged to be at least partially inserted into a slot 228 comprised by the second rotatable gripper hub 204. In an embodiment of the rotation mechanism 200 comprising three gripper units, the second rotatable gripper hub 202 thus comprises three slots 228. A slot 228 allows a second protrusion 226 to slide in-between two positions constrained by the slot 228.

The configuration of the first protrusion 222 and hole 224 provides that a gripping unit such as the first gripping unit 210 is rotatably connected to the first gripper hub 202. The configuration of the second protrusion 226 and the slot 228 provides that a gripping unit such as the first gripping unit 210 is slidably connected to the second gripping hub 204.

Different embodiments of the rotation mechanism 200 are envisioned wherein a first of the first rotatable gripper hub 202, the second rotatable gripper hub 204, and the gripper units comprises one or more holes 224. Furthermore, a second of the first rotatable gripper hub 202, the second rotatable gripper hub 204, and the gripper units comprises one or more slots 228. Additionally, a third of the first rotatable gripper hub 202, the second rotatable gripper hub 204, and the gripper units comprises one or more first protrusions 222. Also, and a fourth of the first rotatable gripper hub 202, the second rotatable gripper hub 204, and the gripper units comprises one or more second protrusions 226. In this embodiment, the gripper units comprise two of the one or more holes 224, one or more slots 228, one or more first protrusions 222 and one or more second protrusions 226.

In another embodiment of the device 100, the first gripping unit 210, the second gripping unit 212 and optional third gripping unit 214 are slidably mounted to a first of the first gripper hub 202 and the second gripper hub 204 such that a substantially straight and racially oriented sliding trajectory is provided when the first gripper hub 202 is rotated relative to the second gripper hub 204. The first gripping unit 210, the second gripping unit 212 and optional third gripping unit 214 furthermore are slidably mounted to a second of the first gripper hub 202 and the second gripper hub 204 such that a curved substantially eccentric trajectory is provided when the first gripper hub 202 is rotated relative to the second gripper hub 204.

When the gripping sections 216 engage with the object they cannot move further towards the axis of rotation 201, assuming the object has a substantially high stiffness such that the object may substantially not be deformed, elastically and/or plastically, due to the gripping sections 216 engaging with the object.

The controller 130 may be arranged to, for example during the first operating step, operate the one of the first driving unit 112 and the second driving unit 114 in a first direction for moving the gripper units 216, preferably substantially racially, towards the axis of rotation 201 by a pre-determined distance. Such a pre-determined distance may be determined based on a slicing distance of the second protrusions 226 in the slots 228. A too large distance for the gripping sections 216 may result in failure of the second protrusions 226 if they engage an end of a slot 228 before the pre-determined distance has been reached.

The device 100 may comprise a torque sensing module for determining a torque applied by the one of the first driving unit 112 and the second driving unit 114. The torque sensing module may send a signal comprising information of the sensed torque to the controller 130 which may be arranged to receive the signal. In an embodiment of the device 100 comprising the torque sensing module, the controller 130 may be arranged to operate the one of the first driving unit 112 and the second driving unit 114 in the first direction for moving the gripper units 216 towards the axis of rotation 201 until the torque reaches a pre-determined value.

The pre-determined torque value may be reached due to the gripping sections 216 engaging with the object that is to be rotated. Stopping the rotation of the one of the first driving unit 112 and the second driving unit 114 prevents the gripping sections 216 from at least one of damaging the object, overloading the one of the first driving unit 112 and the second driving unit 114, or damaging parts of the device 100 such as the first gripper hub 202, second gripper hub 204, gripper units and/or gripping sections 216.

The device 100 may further comprise a memory for storing an amount of rotational movement of the one of the first driving unit 112 and the second driving unit 114 until the torque reaches the pre-determined value. The amount of rotational movement may correspond to a distance between the gripping sections 216 and the axis of rotation 201 and in turn may correspond to a diameter or size of the object that is inserted into the device 100. Storing the amount of rotational movement may give an indication of the amount of objects that have been rotated by the device 100, and the size of the rotated objects. This amount may furthermore be used to give an indication of the amount of objects present in the container 108, and may give an indication whether the container 108 is full or almost full and needs to be replaced.

The first driving unit 112 and the second driving unit 114 may be powered by the electricity grid, and/or may be provided with a battery such that the device 100 does not depend on the presence of an electricity grid to be used.

To drive the first gripper hub 202 with the first driving unit 112, the first gripper hub 202 may comprise an outer circumference with provided thereon a circular rack and the first driving unit 112 may be provided with a gear with teeth corresponding to the circular rack of the first gripper hub 202. Corresponding shape of the gears, such as a straight or helical shape and pitch allow the first driving unit 112 to engage with the first gripper hub 202 and transfer a rotation.

Alternatively, the rotation of the first driving unit 112 may be transferred to the first gripper hub 202 using a belt, toothed belt, or with direct frictional contact between the first gripper hub 202 and first driving unit 112. Similarly, the rotation of the second driving unit 114 may be transferred to the second gripper hub 204.

In an embodiment of the device 100, at least one of the first driving unit 112 and the second driving unit 114 is arranged to engage with the first gripper hub 202 and the second gripper hub 204, respectively, via a biasing element 290. The biasing element 290 is arranged such that the gripping sections 216 are biased away from the axis of rotation 201. This causes the gripping sections 216 to be biased into an open position, arranged for receiving the object. If no torque, or less torque than the torque required for biasing, is provided by the at least one of the first driving unit 112 and the second driving unit 114, the gripping sections 216 may return to this open position by virtue of the biasing element 290. The no torque, or less torque than required for biasing, may be provided intentionally, or may occur due to a failure to deliver power to the at least one of the first driving unit 112 and the second driving unit 114. Such an embodiment of the device 100 comprising the biasing element 290 may not need a controller 130 which is arranged to perform the third operating step, as discussed earlier-on.

The biasing element 290 may be a spring optionally provided between the at least one of the first driving unit 112 and the second driving unit 114 and the first gripper hub 202 and the second gripper hub 204, respectively. The spring may be arranged as a torsion spring, a coil spring provided at a radius from the axis of rotation 201, or any other type of spring. Optionally, the biasing element 290 may be provided with a dampening element, arranged to control and/or limit the speed at which the biasing element 290 may rotate the at least one of the first gripper hub 202 and the second gripper hub 204.

Rotating the first gripper hub 202 and the second gripper hub 204 at the same or substantially the same annular speed allows the gripping sections 216 to rotate without the gripping sections 216 moving radially relative to the axis of rotation 201. This in turn allows the object to rotate around the axis of rotation 201 together with the gripping sections 216 that grip the object. In the example where the object comprises a needle screwed onto a syringe, the needle may be gripped by the device 100 and the syringe may be held by a user, such as a surgeon, nurse, dentist or assistant, preferably using only one hand leaving the other hand free to use for another task. When the needle is rotated relative to the syringe in the second step, the needle may be screwed off the needle and the user is left with only the syringe in his hand.

In another embodiment of the device, a biasing element 290 is provided between at least one of the driving units and the corresponding gripper hub such that the gripping sections 216 are biased to a closed position. The biasing element 290 may be provided in a way similar as discussed with the embodiment discussed above, yet in an opposite fashion. In a preferred embodiment, the biasing element 290 is provided such that movement is limited in both directions. In this way, the gripping units 216 may be moved to a position in which they are arranged to receive an object, such as a needle.

Upon a closing movement of the gripping units 216, the gripping units 216 abut to the needle. Due to the presence of the biasing element 290, further movement of the first gripper hub 202 relative to the second gripper hub 204 is possible. With such further movement, force applied by the biasing element 290 increases, which force is transferred to the grippers as a force applied to the needle. This improves grip of the grippers on the needle. With this embodiment, movement of the driving units for gripping a needle or needle cuff does not have to be controlled in an exact way to properly grip the needle. Additional movement is even preferred, as the driving unit, in particular when embodied as a stepper motor, increases in that way a force exerted on the needle, via the spring as a biasing element.

If the device 100 is intended to be used for medical applications, parts of the device 100, such as the rotation mechanism 200, which come into contact with the object, may be arranged to be cleaned in an autoclave. Materials comprised by these parts of the device 100 may be chosen accordingly to withstand the temperature, humidity and/or pressure of an autoclave.

Stabbing accidents are prone to occur to people handling needles, for example when recapping a needle or when trying to remove a needle from a syringe. In summary, a device may be provided for safe and automatic removal of a needle from a syringe aimed to prevent stabbing accidents. The device is arranged to grab hold of and rotate the needle of a syringe. The needle, after being rotate off the syringe is discarded into the device by releasing the grip on the needle. The device rotates two rotating gears relative to each other to move grippers towards the needle, and rotates the two gears together to rotate the needle relative to the syringe which may be held by the user.

In the description above, it will be understood that when an element such as layer, region or substrate is referred to as being "on" or "onto" another element, the element is either directly on the other element, or intervening elements may also be present. Also, it will be understood that the values given in the description above, are given by way of example and that other values may be possible and/or may be strived for.

Furthermore, the invention may also be embodied with less components than provided in the embodiments described here, wherein one component carries out multiple functions. Just as well may the invention be embodied using more elements than depicted in the Figures, wherein functions carried out by one component in the embodiment provided are distributed over multiple components.

It is to be noted that the figures are only schematic representations of embodiments of the invention that are given by way of non-limiting examples. For the purpose of clarity and a concise description, features are described herein as part of the same or separate embodiments, however, it will be appreciated that the scope of the invention may include embodiments having combinations of all or some of the features described. The word 'comprising' does not exclude the presence of other features or steps than those listed in a claim. Furthermore, the words 'a' and 'an' shall not be construed as limited to 'only one', but instead are used to mean 'at least one', and do not exclude a plurality.

A person skilled in the art will readily appreciate that various parameters and values thereof disclosed in the description may be modified and that various embodiments disclosed and/or claimed may be combined without departing from the scope of the invention.

It is stipulated that the reference signs in the claims do not limit the scope of the claims, but are merely inserted to enhance the legibility of the claims.

The invention claimed is:

1. A device for rotating a needle off of a syringe, the device comprising a rotation mechanism comprising:
   a first rotatable gripper hub arranged to be driven by a first driving unit comprised by the device, the first gripper hub having a first central opening and the first gripper hub being arranged to be rotated around an axis of rotation;
   a second rotatable gripper hub arranged to be driven by a second driving unit comprised by the device, the second gripper hub having a second central opening aligned with the first central opening and the second gripper hub being arranged to be rotated around the axis of rotation;
   a first gripper unit having a first gripping section for engaging with the needle and a second gripper unit having a second gripping section for engaging with the needle,
      wherein the first gripper unit and the second gripper unit are mounted to the first gripper hub and the second gripper hub such that if the first gripper hub is rotated relative to the second gripper hub, the first and second gripping sections move towards the axis of rotation, and
      wherein the first gripper unit and the second gripper unit are rotatably connected to a first of the first gripper hub and the second gripper hub and slidably connected to a second of the first gripper hub and the second gripper hub; and
   a controller arranged to:
      operate one of the first driving unit and the second driving unit such that the first gripper hub is rotated relative to the second gripper hub in a first direction for moving the first gripping section and the second gripping section towards the axis of rotation; and
      operate the first driving unit and the second driving unit such that the first gripper hub and the second gripper hub rotate at substantially the same annular speed around the axis of rotation.

2. The device according to claim 1, wherein the controller is further arranged to operate one of the first driving unit and the second driving unit such that the first gripper hub is rotated relative to the second gripper hub in a second direction for moving the first gripping section and the second gripping section substantially radially away from the axis of rotation.

3. The device according to claim 1, wherein at least one of the first driving unit and the second driving unit is arranged to engage with the first gripper hub and the second gripper hub, respectively, via a biasing element, such that the first and second gripping sections are biased away from the axis of rotation.

4. The device according to claim 3, wherein the biasing element is a spring operationally provided between the at least one of the first driving unit and the second driving unit and the first gripper hub and the second gripper hub, respectively.

5. The device according to claim 3, wherein the at least one of the first driving unit and the second driving unit is arranged to drive a gear and is connected to the gear through the biasing element and the corresponding gripper hub of the at least one of the first driving unit and the second driving unit arranged to drivie the gear is provided with a circular rack arranged to engage with the gear.

6. The device according to claim 1, wherein the controller is arranged to operate the one of the first driving unit and the second driving unit in the first direction for moving the first gripping section and the second gripping section towards the axis of rotation by a pre-determined distance.

7. The device according to claim 1, wherein:
   the device comprises a torque sensing module for determining a torque applied by the one of the first driving unit and the second driving unit; and
   the controller is arranged to operate the one of the first driving unit and the second driving unit in a first direction for moving the first gripping section and the second gripping section towards the axis of rotation until the torque reaches a predetermined value.

8. The device according to claim 7, further comprising a memory for storing an amount of rotational movement of the one of the first driving unit and the second driving unit until the torque reaches the predetermined value.

9. The device according to claim 1, wherein when the first driving unit and the second driving unit are operated such that the first gripper hub and the second gripper hub move at substantially the same annular speed, the first gripper hub and the second gripper hub move in the first direction.

10. The device according to claim 1, wherein the device further comprises a sensor for detecting if a needle has been provided to the device.

11. The device according to claim 1, wherein at least one of the first rotatable gripper hub and the second rotatable gripper hub comprises a cavity to accommodate at least part of the first gripper unit or the second gripper unit.

12. The device according to claim 1, wherein the first gripper unit and the second gripper unit are positioned between the first rotatable gripper hub and the second rotatable gripper hub.

* * * * *